United States Patent [19]
Tybinkowski et al.

[11] Patent Number: 5,937,028
[45] Date of Patent: Aug. 10, 1999

[54] ROTARY ENERGY SHIELD FOR COMPUTED TOMOGRAPHY SCANNER

[75] Inventors: Andrew P. Tybinkowski, Boxford; Michael J. Duffy, Methuen; Gilbert W. McKenna, Revere, all of Mass.

[73] Assignee: Analogic Corporation, Peabody, Mass.

[21] Appl. No.: 08/948,698

[22] Filed: Oct. 10, 1997

[51] Int. Cl.⁶ .................................................. G01N 23/00
[52] U.S. Cl. ............................................. 378/203; 378/4
[58] Field of Search ................................... 378/203, 4

[56] References Cited

U.S. PATENT DOCUMENTS 5,724,400  3/1998  Swerdloff et al. ..................... 378/65
5,818,897  10/1998  Gordon ..................................... 378/4

Primary Examiner—David P. Porta
Assistant Examiner—Drew A. Dunn
Attorney, Agent, or Firm—Lappin & Kusmer LLP

[57] ABSTRACT

In a computed tomography (CT) scanner, an X-ray shield is mountable to a gantry for absorbing randomly scattered X-ray radiation. The shield is rotatable with the gantry disk for regulating the emission of X-ray radiation near its source. The shield is preferably lined with an energy-absorbent material to provide safe energy levels in the environment external to the system. By minimizing the surface area of the shield, the present system results in significant weight reduction and ease of installation over prior shielding systems.

19 Claims, 3 Drawing Sheets

ROTARY ENERGY SHIELD FOR COMPUTED TOMOGRAPHY SCANNER

RELATED APPLICATIONS

This application is related to the following U.S. applications filed on even date herewith, of common assignee, the contents of which are incorporated herein in their entirety by reference:

"Computed Tomography Scanner Drive System and Bearing," invented by Andrew P. Tybinkowski, et al., (Attorney Docket No. ANA-128);

"Air Calibration Scan for Computed Tomography Scanner with Obstructing Objects," invented by David A. Schafer, et al., (Attorney Docket No. ANA-129);

"Computed Tomography Scanning Apparatus and Method With Temperature Compensation for Dark Current Offsets," invented by Christopher C. Ruth, et al., (Attorney Docket No. ANA-131);

"Computed Tomography Scanning Target Detection Using Non-Parallel Slices," invented by Christopher C. Ruth, et al., (Attorney Docket No. ANA-132);

"Computed Tomography Scanning Target Detection Using Target Surface Normals," invented by Christopher C. Ruth, et al., (Attorney Docket No. ANA-133);

"Parallel Processing Architecture for Computed Tomography Scanning System Using Non-Parallel Slices," invented by Christopher C. Ruth, et al., (Attorney Docket No. ANA-134); "Computed Tomography Scanning Apparatus and Method Generating Parallel Projections Using Non-Parallel Slices," invented by Christopher C. Ruth, et al., (Attorney Docket No. ANA-135);

"Computed Tomography Scanning Apparatus and Method Using Adaptive Reconstruction Window," invented by Bernard M. Gordon, et al., (Attorney Docket No. ANA-136);

"Area Detector Array for Computed Tomography Scanning System," invented by David A. Schafer, et al., (Attorney Docket No. ANA-137);

"Closed Loop Air Conditioning System for a Computed Tomography Scanner," invented by Eric Bailey, et al., (Attorney Docket No. ANA-138);

"Measurement and Control System for Controlling System Functions as a Function of Rotational Parameters of a Rotating Device," invented by Geoffrey A. Legg, et al., (Attorney Docket No. ANA-139).

BACKGROUND OF THE INVENTION

In modern computed tomography (CT) scanner systems of the third generation type, an X-ray source and detector array rotate about a subject or object to be scanned. During a scan, the source and detectors image the object at incremental scan angles. A process referred to as reconstruction generates a series of two-dimensional images or slices of the object from the captured data.

The source, detectors, and related components are mounted to a rotatable gantry supported by a rigid stationary frame. As the gantry rotates, a conveyor passing transversely through a central aperture in the gantry translates the object relative to the sensors. The X-ray source generates an electromagnetic energy beam which is attenuated by the object as the beam propagates to the detector array. Each time a beam is fired at the object, X-ray reflections scatter throughout the system housing.

In these systems, environmental safety is of utmost concern as exposure to X-ray energy is known to be harmful to humans. In current CT scanner embodiments, the entire scanner housing is lined with lead for absorbing X-ray energy to prevent emission into the environment external to the housing.

FIG. 1 is a cutaway side view of an X-ray shield configuration in accordance with the prior art. An X-ray source 20 and detectors 24 are mounted on a rotatable gantry 21. The X-ray source 20 generates a beam 26 which is directed toward detectors 24. A conveyor 32 introduces an object 36 into the path of the beam 26 which attenuates the beam and further causes the beam 26 to scatter throughout the conveyor tunnel area 46 and throughout the system within housing 22. A lead lining 34 is provided throughout the inner surface of the housing, and lead curtains 30 are provided in tunnel 46, to prevent scattered X-rays 28 from radiating into the environment external to the housing 22, protecting a human operator 44 from prolonged exposure to X-rays of otherwise released energy 38. The lead lining 34 must be sufficiently thick, for example 2.5 mm, to absorb and/or attenuate scattered beams 28, and therefore can add thousands of pounds to the system weight. Furthermore application of the lining 34 is tedious, resulting in high installation costs.

SUMMARY OF THE INVENTION

The present invention is directed to an X-ray shield which overcomes the limitations of the prior art. Specifically, the present invention comprises a shield mounted to the gantry and rotatable therewith for absorbing randomly-directed X-rays. It is therefore unnecessary to line the entire surface of the system housing with lead as in prior art systems. This configuration results in a shielding system which is significantly reduced in weight and installation costs: the shield is designed to encompass only those areas where the active X-rays are required for system operation, shielding the remainder of the system and the external environment from harmful radiation.

The apparatus of the invention comprises an energy shield for a computed tomography scanning system for confining radiant X-ray energy to a volume within the shield. The shield is mountable to a gantry rotatable relative to a fixed frame. The gantry includes an X-ray beam source and detector array on opposite sides of a central gantry aperture. The shield is rotatable with the gantry about an object to be scanned positioned in the aperture. The shield is lined with a material absorbent of X-ray energy incident thereon during a tomographic scan.

In a preferred embodiment, the absorbent material comprises lead sheeting, and the shield is formed of sheet metal, for example sheet steel or stainless steel. A flange is included to shield the seam area formed between the rotatable gantry and the fixed frame.

BRIEF DESCRIPTION OF THE DRAWINGS

The foregoing and other objects, features and advantages of the invention will be apparent from the more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF PREFERRED EMBODIMENTS

Figure 1:
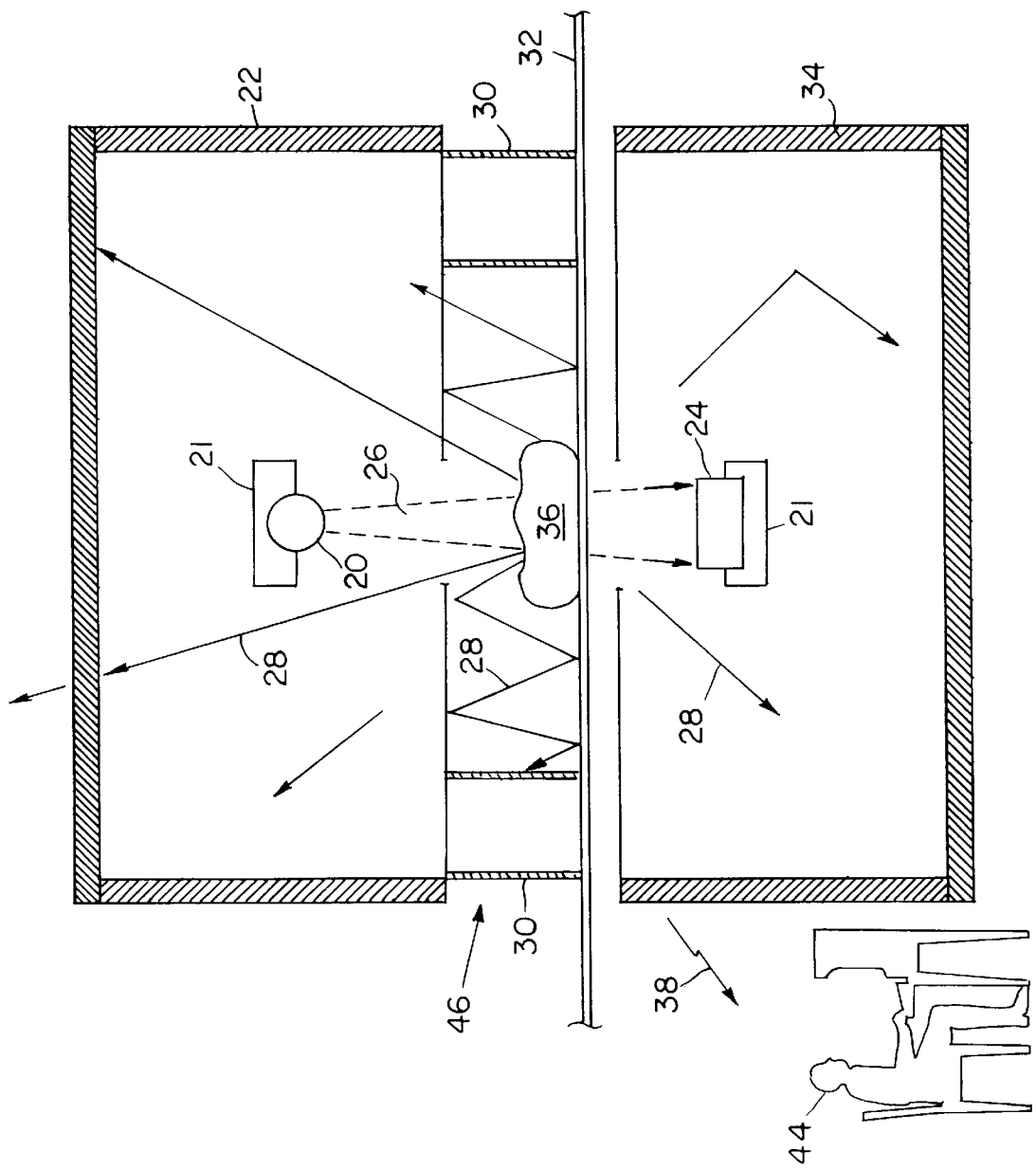
FIG. 1 is a cutaway side view of a prior art CT scanner configuration for shielding scattered X-ray energy.
Figure 2:
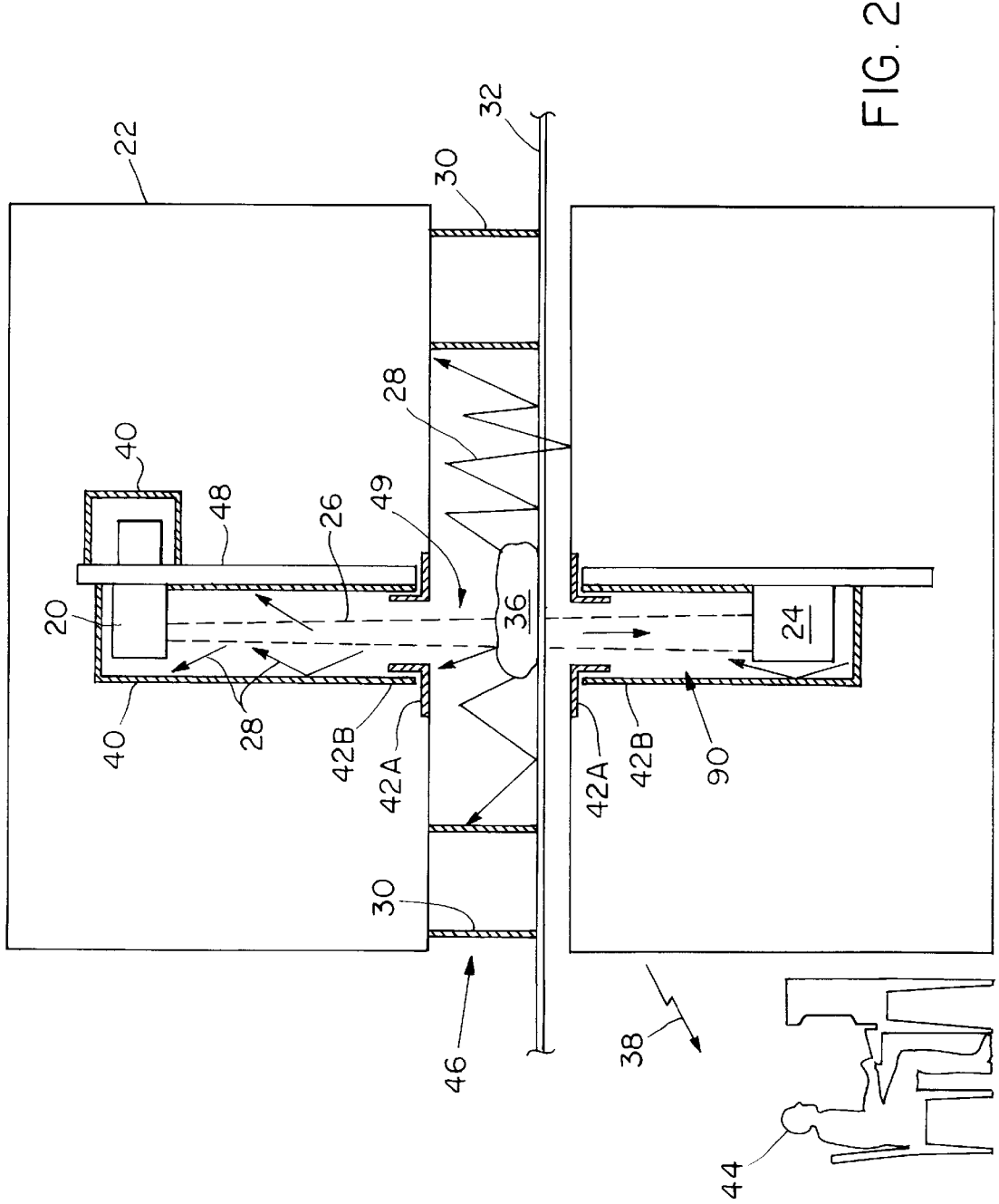
FIG. 2 is a cutaway side view of an X-ray shielding configuration in accordance with the present invention.

The present invention is directed to an improved X-ray shield apparatus mountable and rotatable with a CT scanner gantry. In the improved configuration of FIG. 2, a gantry disk 48 is mounted to a fixed, stationary frame (not shown) enclosed within a frame housing 22. The gantry disk 48 is rotatable about an object 36 transversely transported through a tunnel 46 by conveyor 32. The disk 48 includes a central aperture 49, allowing the object 36 to pass therethrough during a tomographic scan.

Components, including X-ray source 20 and detector array 24, are mounted to the gantry disk 48. The source 20 generates X-ray energy which is incident on the object 36. Some of the incident energy is scattered into beams 28 radiating in all directions. In accordance with the present invention, a shield 40 mounted to the gantry disk 48 and rotatable therewith prevents reflected beams 28 from exiting the beam interrogation area 90, while leaded curtains 30 prevent reflected beams 28 from exiting the tunnel area 46, thereby protecting an operator 44 or other nearby human from exposure to otherwise released energy 38.

In a preferred embodiment, the shield 40 comprises sheet metal, for example sheet steel or stainless steel lined with 2.5 mm thick lead sheeting. In accordance with patent application ANA-128, cited above and filed of even date herewith, components, for example X-ray source 20, may be mounted on both faces of the gantry disk 48 as shown. The shield 40 of the present invention is configured to encapsulate such "hot", i.e. energized, areas on both faces of the gantry disk 48. A flange including a stationary segment 42A mounted at or near tunnel surface 46, and a rotatable segment 42B mounted to the shield 40 is likewise lined with lead to prevent X-rays from passing through the junction of the rotatable gantry and the fixed side of the tunnel 46. The tunnel surface 46 may be lined with lead for absorbing energy beams directed therein.

Figure 3:
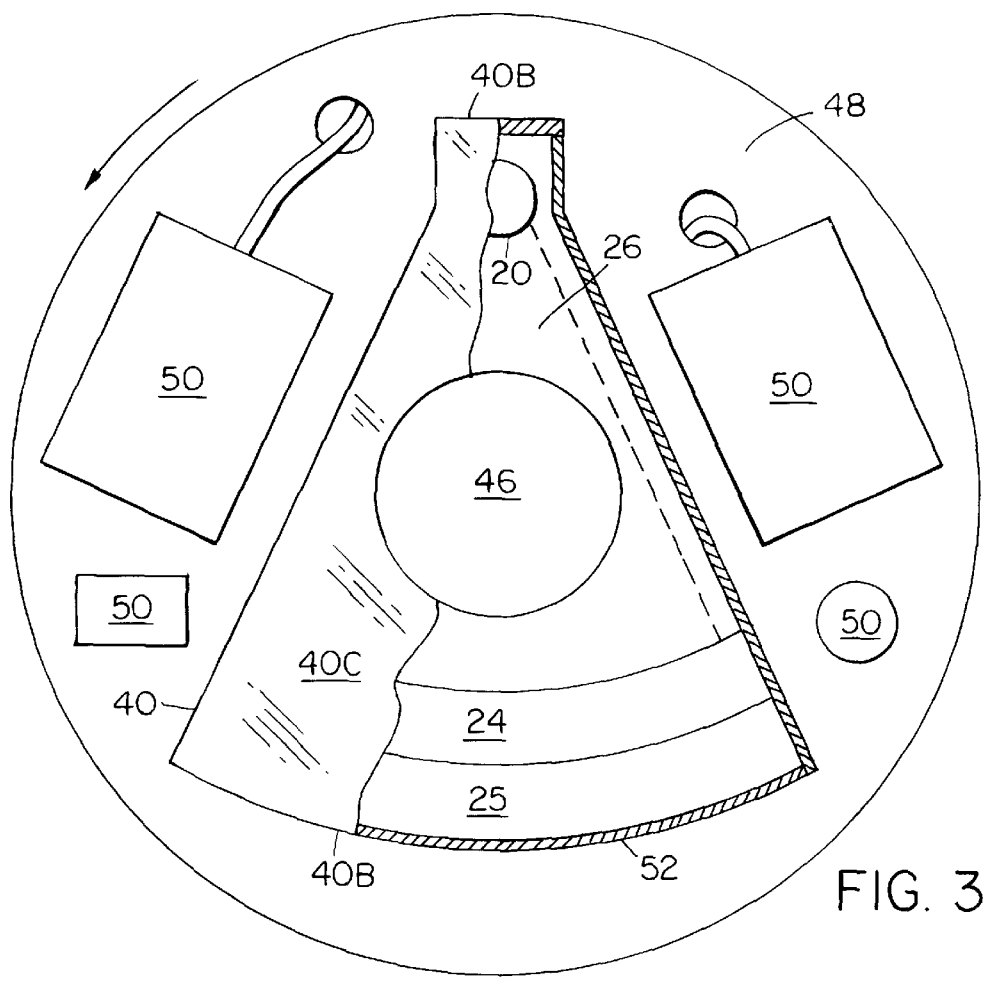
FIG. 3 is a front view of the X-ray shield mounted to a gantry in accordance with the present invention.

FIG. 3 is a front view of the gantry and shield of the present invention. Additional components 50 are likewise mountable to the gantry disk 48 and rotate about the object and aperture 46. In this view it can be seen that the X-ray beam 26 emitted from source 20 passes unhindered through the aperture area 46 to detectors 24. The detector crystals 24 absorb approximately 99% of the X-rays 26 incident thereon. The corresponding data acquisition system 25, designed to interpret the signals captured by the detector crystals 24, is lined on its undersurface 52 to absorb the remaining 1% of the X-rays which pass through the crystals 24. Gantry components 50 including the X-ray, cathode, anode, communication systems, and cooling systems 50 are not encompassed by the shielded area since these components do not generate harmful X-rays. Enclosing only the "hot" areas minimizes the size and therefore the surface area of the shield 40, thereby minimizing its weight.

Figure 4:
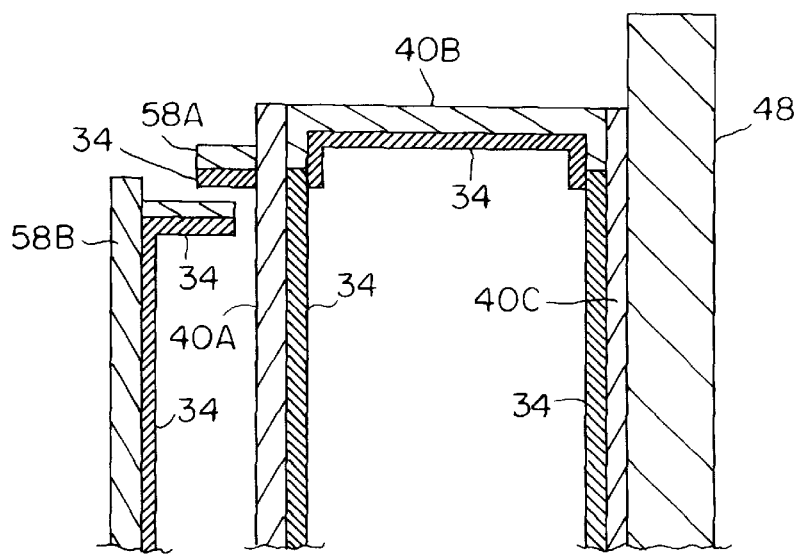
FIG. 4 is a close-up side view of a preferred shield configuration of the present invention.

FIG. 4 is a close-up side view of a preferred shield configuration of the present invention. A preferred shield includes sheet steel sections 40A, 40B, 40C. Portion 40C comprises a flat panel coupled to the surface of gantry disk 48; portion 40B is fabricated in C-channel form and is coupled between sections 40A and face plate 40C as shown. The panels 40A, 40B, 40C may be welded, riveted or otherwise coupled together. The inner surface area of the resulting shield is lined with lead sheeting 34 to provide a primary barrier to harmful X-ray radiation. A flange is formed by interlocking rotatable and fixed collars 58A and 58B, respectively to operate as a secondary barrier to X-ray radiation.

In a preferred experimental embodiment, a rotatable shield in accordance with the present invention was lined with 2.5 mm lead sheeting which weighed, in combination with the sheet metal frame, approximately 200 lbs. This is in contrast with prior art systems which line the interior of the housing 22 at a weight of approximately 1700 lbs due to the larger surface area to be covered by lead shielding. The preferred experimental embodiment exhibited less than 0.5 milliRankin/hr X-ray emissions at 1 inch from the surface of the housing 22; within the Food and Drug Administration specification for proper shielding. Furthermore, the shield of the present invention being more compact and closer to the X-ray source, results in reduced installation expenses for applying lead lining to the shield 40.

While this invention has been particularly shown and described with references to preferred embodiments thereof, it will be understood by those skilled in the art that various changes in form and details may be made therein without departing from the spirit and scope of the invention as defined by the appended claims.

We claim:

1. An energy shield for a computed tomography scanning system for substantial confinement of radiant X-ray energy, said shield being mountable to a gantry rotatable relative to a fixed frame, said gantry including an X-ray beam source and detector array on opposite sides of a central gantry aperture, said shield encompassing a volume defined along the portions of the X-ray beam path between said X-ray beam source and said detector array extending around said aperture and encompassing both said source and said detector said shield being rotatable with said gantry about said aperture, said shield being lined with a material absorbent of X-ray energy incident thereon generated during a tomographic scan.

2. The energy shield of claim 1 wherein said absorbent material comprises lead sheeting.

3. The energy shield of claim 1 wherein the shield comprises sheet metal.

4. The energy shield of claim 1 further comprising a flange formed of a rotatable collar coupled to said shield and a fixed collar coupled to said fixed frame for reducing emission of X-ray energy from said volume.

5. The energy shield of claim 1 further comprising shielding curtains for further confining X-ray energy to a region surrounding said aperture.

6. The energy shield of claim 1 further comprising a stationary shield segment mounted at the edge of said aperture positioned to prevent X-ray energy from passing through the junction of said rotatable gantry and said aperture.

7. The energy shield of claim 1 wherein said gantry comprises a rotatable disk having front and rear surfaces and wherein said shield extends to both front and rear surfaces of said disk.

8. An energy shield for a computed tomography scanning system for confining radiant X-ray energy to a volume within the shield, said shield mountable to a gantry rotatable relative to a fixed frame, said gantry including an X-ray beam source and detector array on opposite sides of a central gantry aperture, said shield rotatable with said gantry about an object to be scanned positioned in said aperture, said shield lined with a material absorbent of X-ray energy incident thereon generated during a tomographic scan, said shield further comprising a flange formed of a rotatable collar coupled to said shield and a fixed collar coupled to said fixed frame for reducing emission of X-ray energy from said volume.

9. The energy shield of claim 8 wherein said absorbent material comprises lead sheeting.

10. The energy shield of claim 8 wherein the shield comprises sheet metal.

11. A computed tomography scanning system comprising:
   an X-ray beam source for generating an X-ray beam along a predefined X-ray beam path;
   a detector array for receiving X-rays emitted from the source along the path during a scan;
   a fixed frame;
   a gantry, rotatably supported by the fixed frame, having a central aperture and supporting at least the X-ray beam source so that the beam rotates about a rotation axis during a scan; and
   a shield for substantial confinement of radiant X-ray energy, said shield being mountable to the gantry for rotation with the gantry, and encompassing a volume defined by the part of the X-ray beam path between said X-ray beam source and said detector array other than substantially the beam portion passing across the aperture and encompassing both said source and said detector, said shield being lined with a material absorbent of X-ray energy incident thereon generated during a scan.

12. The scanning system of claim 11 wherein said absorbent material comprises lead sheeting.

13. The scanning system of claim 11 wherein the shield comprises sheet metal.

14. The scanning system of claim 11 further comprising a flange formed of a rotatable collar coupled to said shield and a fixed collar coupled to said fixed frame for reducing emission of X-ray energy from said volume.

15. The scanning system of claim 11 further comprising shielding curtains for further confining X-ray energy to a region surrounding said aperture.

16. The scanning system of claim 11 further comprising a stationary shield segment mounted at the edge of said aperture positioned to prevent X-ray energy from passing through the junction of said rotatable gantry and said aperture.

17. The scanning system of claim 11 wherein said gantry comprises a rotatable disk having front and rear surfaces and wherein said shield extends around both front and rear surfaces of said disk.

18. The scanning system of claim 11 further including a conveyor for conveying objects through the aperture.

19. The scanning system of claim 11 further comprising shielding curtains for allowing objects on the conveyor to pass through the aperture while further confining X-ray energy to a region surrounding said aperture.

* * * * *